United States Patent
Dwivedi et al.

(10) Patent No.: US 9,840,469 B2
(45) Date of Patent: *Dec. 12, 2017

(54) POLYMORPHIC FORMS OF IVABRADINE HYDROCHLORIDE

(71) Applicant: CADILA HEALTHCARE LIMITED, Gujarat (IN)

(72) Inventors: Shriprakash Dhar Dwivedi, Gujarat (IN); Ashok Prasad, Gujarat (IN); Mukul Hariprasad Sharma, Gujarat (IN); Piyush Rajendra Sharma, Gujarat (IN); Jayprakash Ajitsingh Parihar, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/485,409

(22) Filed: Apr. 12, 2017

(65) Prior Publication Data

US 2017/0217898 A1 Aug. 3, 2017

Related U.S. Application Data

(63) Continuation of application No. 15/168,880, filed on May 31, 2016, now Pat. No. 9,650,344, which is a continuation of application No. 14/818,236, filed on Aug. 4, 2015, now Pat. No. 9,382,209, which is a continuation of application No. 14/358,025, filed as application No. PCT/IN2012/000743 on Nov. 12, 2012, now Pat. No. 9,120,755.

(30) Foreign Application Priority Data

Nov. 14, 2011 (IN) .................... 3214/MUM/2011

(51) Int. Cl.
*C07D 223/16* (2006.01)
*C30B 7/02* (2006.01)
*C30B 29/54* (2006.01)
*B65D 30/08* (2006.01)
*B65D 81/26* (2006.01)
*B65B 31/00* (2006.01)
*B65B 7/02* (2006.01)
*B65B 61/20* (2006.01)

(52) U.S. Cl.
CPC .............. *C07D 223/16* (2013.01); *B65B 7/02* (2013.01); *B65B 31/00* (2013.01); *B65B 61/20* (2013.01); *B65D 31/02* (2013.01); *B65D 81/266* (2013.01); *C30B 7/02* (2013.01); *C30B 29/54* (2013.01); *C07B 2200/13* (2013.01)

(58) Field of Classification Search
CPC ..................................................... C07D 223/16
See application file for complete search history.

(56) References Cited

U.S. PATENT DOCUMENTS

| | | | |
|---|---|---|---|
| 9,120,755 B2 | 9/2015 | Dwivedi et al. | |
| 9,382,209 B2 | 7/2016 | Dwivedi et al. | |
| 9,650,344 B2 | 5/2017 | Dwivedi et al. | |
| 2014/0315890 A1 | 10/2014 | Prohens Lopez et al. | |

FOREIGN PATENT DOCUMENTS

| | | |
|---|---|---|
| CN | 101 805 289 | 8/2010 |
| EP | 1 587 005 | 10/2005 |
| EP | 1 695 709 | 8/2006 |
| EP | 1 695 710 | 8/2006 |
| EP | 1 695 965 | 8/2006 |
| EP | 1 755 287 | 4/2007 |
| EP | 1 775 288 | 4/2007 |
| FR | 2 882 555 | 9/2006 |
| WO | 2008/065681 | 6/2008 |
| WO | 2008/125006 | 10/2008 |
| WO | 2008/146308 | 12/2008 |
| WO | 2010/072409 | 7/2010 |
| WO | 2011/033194 | 3/2011 |
| WO | 2011/098582 | 8/2011 |

OTHER PUBLICATIONS

U.S. Appl. No. 15/168,880, filed May 31, 2016; Dwivedi et al.
U.S. Appl. No. 14/818,236, filed Aug. 4, 2015; Dwivedi et al.
U.S. Appl. No. 14/358,025, filed May 13, 2014; Dwivedi et al.
International Search Report issued in PCT/IN2012/000743, dated May 2, 2013 (9 pages).
Written Opinion issued in PCT/IN2012/000743, dated May 2, 2013 (7 pages).

*Primary Examiner* — Bruck Kifle
(74) *Attorney, Agent, or Firm* — Nixon & Vanderhye P.C.

(57) ABSTRACT

Stable crystalline Form II and stable crystalline Form III of ivabradine hydrochloride and processes for their preparation are disclosed.

16 Claims, 3 Drawing Sheets

POLYMORPHIC FORMS OF IVABRADINE HYDROCHLORIDE

This patent application is a continuation of U.S. application Ser. No. 15/168,880 filed May 31, 2016, which is a continuation of U.S. application Ser. No. 14/818,236, filed Aug. 4, 2015 (now U.S. Pat. No. 9,382,209), which is a continuation of U.S. application Ser. No. 14/358,025, filed May 13, 2014 (now U.S. Pat. No. 9,120,755), which is a National Phase Entry of International Application No. PCT/IN2012/000743, filed Nov. 12, 2012, which designated the U.S. and claims priority to India Application No. 3214/MUM/2011, filed Nov. 14, 2011. The entire contents of each of the above-identified patent applications are incorporated herein by reference.

FIELD OF THE INVENTION

The invention relates to novel polymorphic forms of ivabradine hydrochloride. More particularly, the invention relates to stable crystalline Form II and stable crystalline Form III of ivabradine hydrochloride and processes for their preparation. Further, the invention also relates to pharmaceutical compositions that include the stable crystalline Form II and the stable crystalline Form III of ivabradine hydrochloride.

BACKGROUND OF THE INVENTION

Ivabradine hydrochloride, 3-{3-[{[(7S)-3,4-dimethoxybicyclo[4.2.0]octa-1,3,5-trien-7-yl] methyl}(methyl)amino]-propyl}-7,8-dimethoxy-1,3,4,5-tetrahydro-2H-3-benzazepin-2-one hydrochloride of Formula (I) has very valuable pharmacological and therapeutic properties, especially bradycardic properties, making it useful in the treatment or prevention of various clinical situations of myocardial ischemia such as angina pectoris, myocardial infarct and associated rhythm disturbances, and also of various pathologies involving rhythm disturbances, especially supraventricular rhythm disturbances, and in the treatment of heart failure.

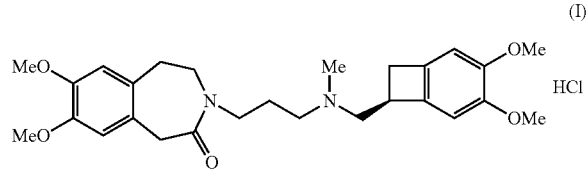 [SMILES: COc1cc2c(cc1OC)CC(=O)N(CCCN(C)C[C@H]1Cc3cc(OC)c(OC)cc31)CC2 ; Cl]

(I)

The preparation and therapeutic use of ivabradine and salts thereof with a pharmaceutically acceptable acid, and especially its hydrochloride, have been described in the European Patent EP 0534859. The patent describes the synthesis of ivabradine hydrochloride by reacting the compound of Formula (V-a) with the compound of Formula (IV-a):

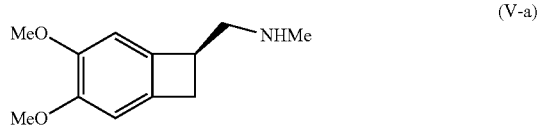

(V-a)

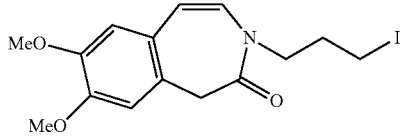

(IV-a)

to give a compound of Formula (II-a), the catalytic hydrogenation of which results in ivabradine, which is then converted into its hydrochloride:

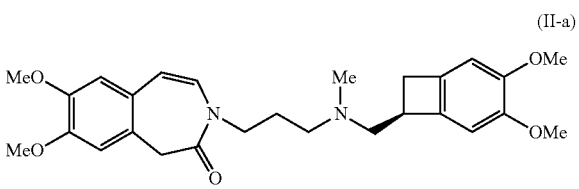 [SMILES: COc1cc2c(cc1OC)CC(=O)N(CCCN(C)C[C@H]1Cc3cc(OC)c(OC)cc31)C=C2]

(II-a)

The disclosed process yielding ivabradine hydrochloride in only a very low yield-less than 17% over the 3 steps as a whole.

Another process for preparing ivabradine is disclosed in U.S. Pat. No. 5,296,482. According to the process, (+)-isomer of ivabradine is treated with aqueous HCl and then recrystallization in acetonitrile leads to the formation of ivabradine hydrochloride salt having m.p. 135-140° C.

International (PCT) Publication WO 2008/146308 A2 discloses process for the preparation of ivabradine hydrochloride by treating ivabradine with alcoholic hydrogen chloride. The specification also discloses the amorphous form of ivabradine hydrochloride and process for its preparation using suitable acid addition salts of ivabradine.

International (PCT) Publication WO 2008/065681 A2 discloses a process for the preparation of ivabradine or the pharmaceutically acceptable salts thereof which is incorporated herein as a reference in its entirety.

International (PCT) Publication WO 2008/125006 A1 discloses a process for the preparation of a crystalline form of ivabradine or the pharmaceutically acceptable salts thereof which is incorporated herein as a reference in its entirety.

International (PCT) Publication WO 2011/098582 A2 discloses three crystalline forms of ivabradine hydrochlorides like Form X, Form Z and Form K, which are incorporated herein as a reference in its entirety.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid-state forms of a drug, including all polymorphic forms, and to determine the stability, dissolution and flow properties of each polymorphic form. The polymorphic forms of a compound can be distinguished in a laboratory by X-ray diffraction spectroscopy and by other methods such as, infrared spectrometry. For a general review of polymorphs and the pharmaceutical applications of polymorphs, See G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

Several crystalline forms of ivabradine hydrochloride and their processes for preparation have been disclosed, for example in U.S. Pat. Nos. 7,176,197 B2, 7,384,932 B2, 7,361,652 B2, 7,361,651 B2, 7,361,650 B2, 7,361,649 B2, and 7,358,240 B2.

The known crystalline forms of ivabradine hydrochloride are pseudopolymorphs, which are very susceptible in presence of water. They are either hydrates like hemihydrate, monohydrate or tetrahydrate or anhydrous compounds. Therefore, the present invention provides new crystalline form of ivabradine hydrochloride, which is stable and useful for pharmaceutical compositions that include the crystalline ivabradine hydrochloride.

SUMMARY OF THE INVENTION

The inventors have discovered novel crystalline polymorphic forms of ivabradine hydrochloride and have developed processes for the preparation of the crystalline forms. The new crystalline forms of ivabradine hydrochloride are designated as Form II and Form III.

In one general aspect there are provided novel crystalline Form II and crystalline Form III of ivabradine hydrochloride.

The Form II of ivabradine hydrochloride may have the X-ray diffraction pattern of FIG. 1 and differential scanning calorimetry thermogram of FIG. 2. The Form III of ivabradine hydrochloride may have the X-Ray diffraction pattern of FIG. 3.

In one general aspect there is provided a process for the preparation of crystalline Form II of ivabradine hydrochloride. The process includes providing a solution of ivabradine hydrochloride in one or more organic solvents to obtain ivabradine hydrochloride solution; and obtaining the crystalline Form II of ivabradine hydrochloride by the removal of solvents.

In another general aspect there is provided a process for the preparation of crystalline Form III of ivabradine hydrochloride. The process includes contacting ivabradine hydrochloride with a preheated one or more suitable solvent to obtain ivabradine hydrochloride solution; and obtaining the crystalline Form III of ivabradine hydrochloride by the removal of solvents.

Removing the solvents may include, for example, one or more of filtration, filtration under vacuum, decantation, centrifugation, distillation, and distillation under vacuum.

Embodiments of the process may include one or more of the following features. For example, the solution of ivabradine hydrochloride may be provided by heating ivabradine hydrochloride in one or more organic solvents. The solution may be seeded with one or more crystals of Form II or Form III of ivabradine hydrochloride prior to the initiation of product crystallization or the slurry may be cooled prior to filtration.

The process may include further drying of the product obtained. The process may include further forming of the product so obtained into a finished dosage form.

In another general aspect there is provided a pharmaceutical composition that includes a therapeutically effective amount of the crystalline Form II or crystalline Form III of ivabradine hydrochloride; and one or more pharmaceutically acceptable carriers, excipients or diluents.

In another general aspect there is provided a pharmaceutical composition comprising crystalline Form II of ivabradine hydrochloride substantially free of one or more of its corresponding impurities as measured by HPLC.

In another general aspect there is provided a pharmaceutical composition comprising crystalline Form III of ivabradine hydrochloride substantially free of one or more of its corresponding impurities as measured by HPLC.

In another general aspect there is provided a stable crystalline Form II of ivabradine hydrochloride which is substantially free from known crystalline forms β, δ, or γ or amorphous form.

In another general aspect there is provided a stable crystalline Form II of ivabradine hydrochloride having water content from about 2.0% to about 4.0% w/w.

In another general aspect there is provided a stable crystalline Form III of ivabradine hydrochloride which is substantially free from known crystalline forms β, δ, or γ or amorphous form.

In another general aspect there is provided a crystalline ivabradine hydrochloride having particle size distributions wherein the $10^{th}$ volume percentile particle size (D10) is less than about 50 μm, the $50^{th}$ volume percentile particle size (D50) is less than about 200 μm, or the $90^{th}$ volume percentile particle size (D90) is less than about 400 μm, or any combination thereof, wherein the crystalline ivabradine hydrochloride may be crystalline Form-II or crystalline Form-III.

The details of one or more embodiments of the inventions are set forth in the description below. Other features, objects and advantages of the inventions will be apparent from the description.

DETAILED DESCRIPTION OF THE INVENTION

Figure 1:
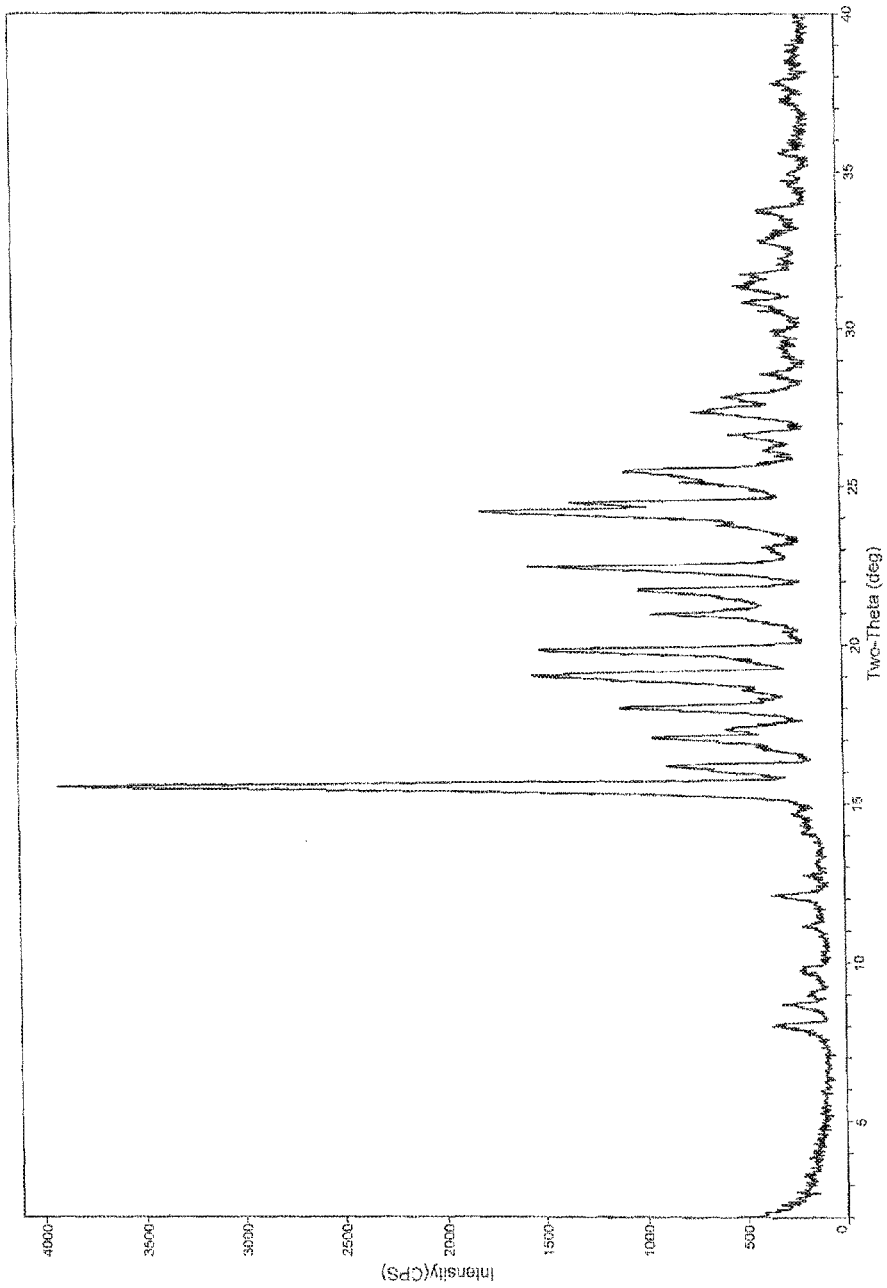
FIG. 1 is an X-ray powder diffraction pattern of crystalline ivabradine hydrochloride Form II.
Figure 2:
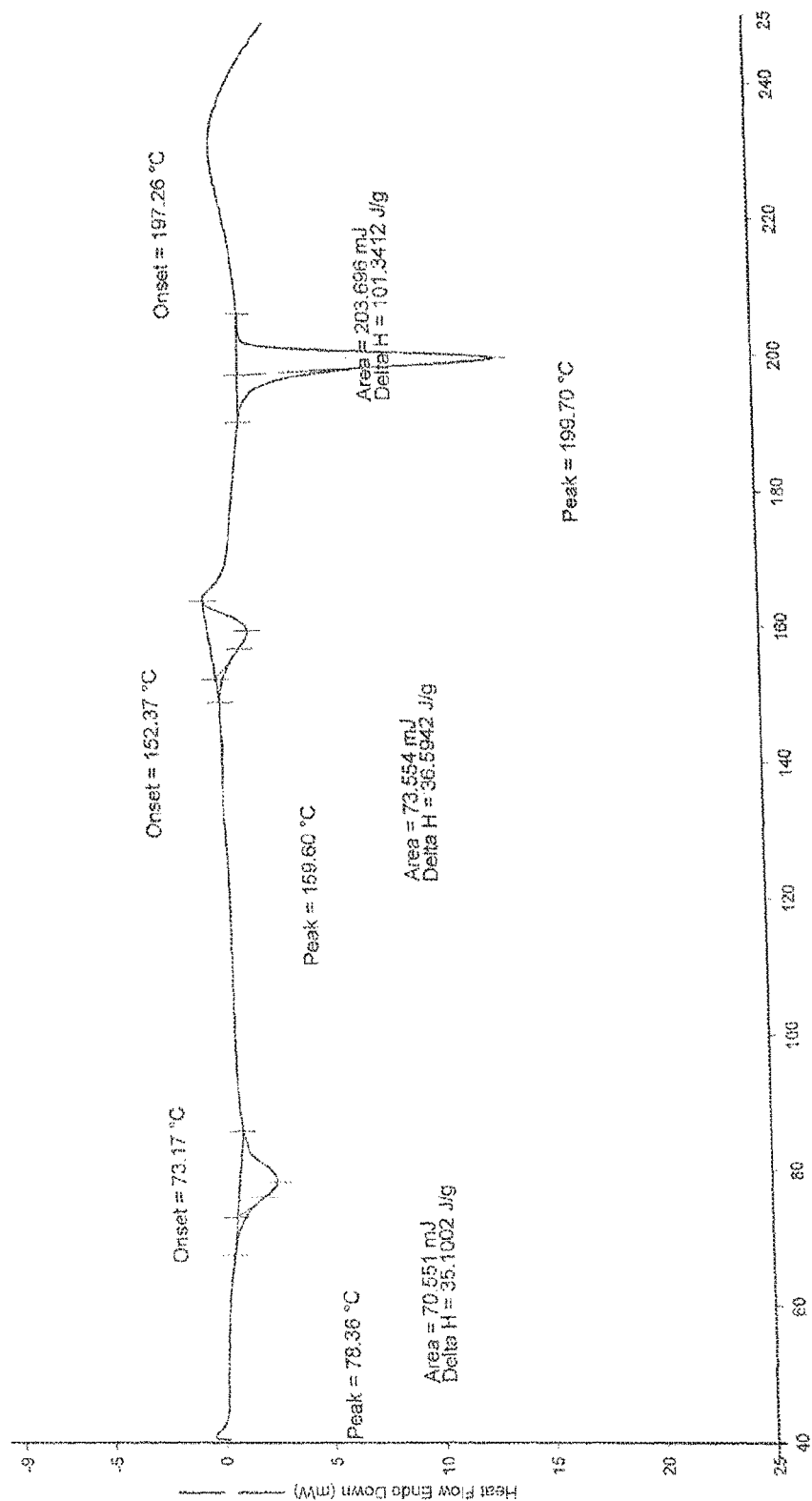
FIG. 2 is a Differential Scanning Calorimetry analysis of crystalline ivabradine hydrochloride Form II.
Figure 3:
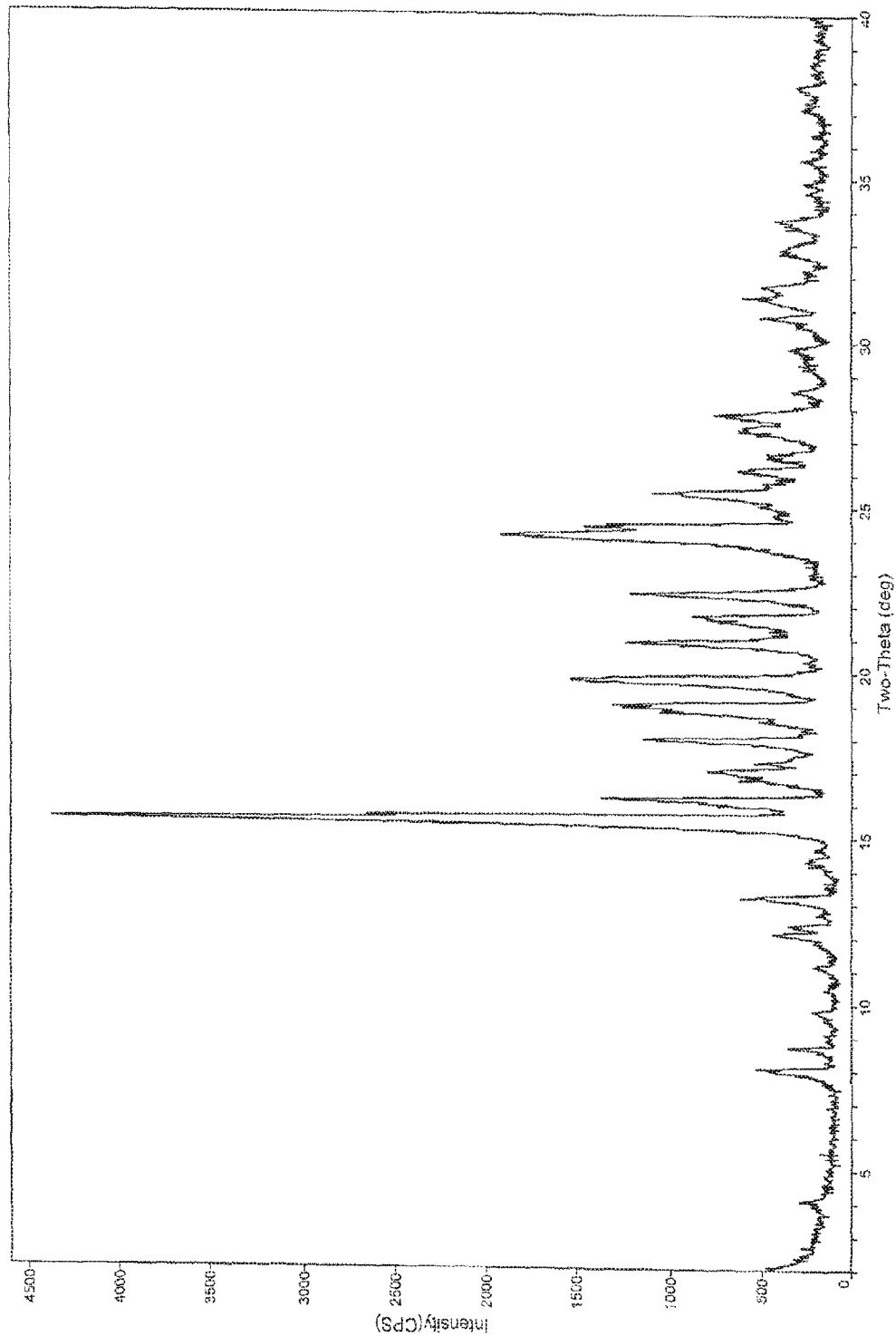
FIG. 3 is an X-ray powder diffraction pattern of crystalline ivabradine hydrochloride Form III.

The inventors have found new polymorphic forms of ivabradine hydrochloride and, in particular, the crystalline forms are designated as Form II and Form III of ivabradine hydrochloride. The new forms are characterized by their respective X-ray powder diffraction pattern as well as differential scanning calorimetry thermogram, as shown in FIGS. 1, 2, and 3.

The inventors also have developed a process for the preparation of the crystalline Form II of ivabradine hydrochloride, by providing solution of ivabradine hydrochloride in one or more solvents to obtain ivabradine hydrochloride solution; and obtaining crystalline Form II of ivabradine hydrochloride by the removal of solvents.

The inventors have also developed a process for the preparation of the crystalline Form III of ivabradine hydrochloride, by contacting ivabradine hydrochloride with a preheated one or more suitable solvent to obtain ivabradine hydrochloride solution; and obtaining the crystalline Form III of ivabradine hydrochloride by the removal of solvents.

In general, the solution of ivabradine hydrochloride may be obtained by dissolving any known form of ivabradine hydrochloride in a suitable solvent. The solution may be obtained by heating the ivabradine hydrochloride in a solvent. The resultant solution may be clarified to remove foreign particulate matter or treated with charcoal to remove coloring and other related impurities. The solution so obtained may be concentrated to reduce the amount of solvent. The solution may be concentrated by removing the solvent completely to get a residue.

Alternatively, such a solution may be obtained directly from a reaction in which ivabradine hydrochloride is formed. The solvent may be removed by a technique which includes, for example, filtration, filtration under vacuum, decantation, centrifugation, distillation and distillation under vacuum.

The inventors have found that the crystalline Form II of ivabradine hydrochloride is stable and is substantially free from known crystalline forms β, δ, γ, or amorphous form. The stable crystalline Form II of ivabradine hydrochloride has no detectable quantity of crystalline β, δ, γ, or amorphous forms after storage for 6 months at 40° C. and a relative humidity of 75% or at 25° C. and a relative humidity of 60%.

The inventors have found that the crystalline Form III of ivabradine hydrochloride is stable and is substantially free from known crystalline forms β, δ, γ, or amorphous form. The stable crystalline Form III of ivabradine hydrochloride has no detectable quantity of crystalline β, δ, γ, or amorphous forms after storage for 6 months at 40° C. and a relative humidity of 75% or at 25° C. and a relative humidity of 60%.

All ranges recited herein include the endpoints, including those that recite a range "between" two values. The terms such as "about", "general", "substantially" and the like are to be construed as modifying a term or value such that it is not an absolute. Such terms will be defined by the circumstances and the terms that they modify as those terms are understood by those skill in the art. This includes, at the very least, a degree of expected experimental error, technique error and instrument error for a given technique used to measure a value.

Thus, the advantage of the present invention is to provide storage stable crystalline forms of ivabradine hydrochloride which doesn't change to amorphous form and doesn't tend to decrease the water content.

When a molecule or other material is identified herein as "substantially free", it generally means, unless specified otherwise, that the material is about 99% pure or more. In general, this refers to purity with regard to unwanted residual solvents, reaction byproducts, impurities and unreacted starting materials. In the case of substantially free crystalline ivabradine hydrochloride, "free" also means about 99% of one crystalline form free from known crystalline forms, as appropriate or in the case of crystalline solids.

As used herein, stable crystalline Form II includes either: ivabradine hydrochloride that after exposure to a relative humidity of 75% at 40° C. or 60% at 25° C., for a period of at least six months does not contain peaks at about 6.8°, 11.9°, and 15.9° 2θ and having less than about 5% of known crystalline forms like β or δ or γ crystalline forms. In particular, it may contain less than about 1% crystalline forms like β or δ or γ crystalline forms, for example, it may not contain any detectable amount of forms like β or δ or γ crystalline forms.

As used herein, stable crystalline Form III includes either: ivabradine hydrochloride that after exposure to a relative humidity of 75% at 40° C. or 60% at 25° C., for a period of at least six months does not contains peaks at about 6.8° 2θ and having less than about 5% of known crystalline forms like β or δ or γ crystalline forms. In particular, it may contain less than about 1% crystalline forms like β or δ or γ crystalline forms, for example, it may not contain any detectable amount of forms like β or δ or γ crystalline forms.

As used herein, stable crystalline Form II includes either: ivabradine hydrochloride that after exposure to a relative humidity of 75% at 40° C. or 60% at 25° C., for a period of at least six months is having less than about 5% of amorphous form. In particular, it may contain less than about 1% amorphous form, for example, it may not contain any detectable amount of amorphous form.

As used herein, stable crystalline Form III includes either: ivabradine hydrochloride that after exposure to a relative humidity of 75% at 40° C. or 60% at 25° C., for a period of at least six months is having less than about 5% of amorphous form. In particular, it may contain less than about 1% amorphous form, for example, it may not contain any detectable amount of amorphous form.

As used herein, the term "obtaining" may include filtration, filtration under vacuum, centrifugation, and decantation to isolate product. The product obtained may be further or additionally dried to achieve the desired moisture values. For example, the product may be dried in a hot air oven, tray drier, dried under vacuum and/or in a Fluid Bed Drier.

"Suitable solvent" means a single or a combination of two or more solvents. As used herein, the term "contacting" includes mixing, adding, slurrying, stirring, or a combination thereof.

In one general aspect, the invention provides a novel crystalline Form II of ivabradine hydrochloride characterized by X-ray powder diffraction pattern having characteristics peaks at about 15.50°, 18.02°, 19.00°, 19.80°, 22.42°, 24.16°, and 25.46° (2θ).

The crystalline Form II of ivabradine hydrochloride is further characterized by X-ray powder diffraction pattern having peaks substantially as depicted in FIG. 1. The crystalline Form II of ivabradine hydrochloride is further characterized by X-ray powder diffraction pattern having characteristic peaks at degrees 2θ substantially as depicted in Table-1 as herein below.

TABLE 1

Characteristic X-ray Powder Diffraction Pattern Peaks (expressed in 2θ ± 0.2° 2θ) and Relative Intensities of Diffraction Lines for Form II of Ivabradine Hydrochloride

| Degree 2θ ± 0.2° 2θ | I/Io |
| --- | --- |
| 8.05 | 6.6 |
| 8.69 | 4.7 |
| 9.00 | 2.0 |
| 9.83 | 3.2 |
| 11.17 | 2.0 |
| 12.11 | 6.2 |
| 12.73 | 1.3 |
| 14.68 | 1.4 |
| 15.50 | 100.0 |
| 16.18 | 16.8 |
| 17.08 | 19.4 |
| 17.35 | 8.7 |
| 18.02 | 21.9 |
| 19.00 | 31.8 |
| 19.80 | 34.3 |
| 20.96 | 18.6 |

TABLE 1-continued

Characteristic X-ray Powder Diffraction Pattern Peaks (expressed in 2θ ± 0.2° 2θ) and Relative Intensities of Diffraction Lines for Form II of Ivabradine Hydrochloride

| Degree 2θ ± 0.2° 2θ | I/Io |
|---|---|
| 21.72 | 20.5 |
| 22.42 | 32.4 |
| 23.07 | 3.2 |
| 23.78 | 8.3 |
| 24.16 | 40.8 |
| 24.46 | 26.8 |
| 25.14 | 11.1 |
| 25.46 | 21.6 |
| 26.16 | 3.0 |
| 26.60 | 7.1 |
| 27.36 | 12.7 |
| 27.85 | 9.3 |
| 28.57 | 4.1 |
| 29.83 | 2.9 |
| 30.82 | 5.5 |
| 31.32 | 6.8 |
| 31.70 | 5.2 |
| 32.76 | 4.1 |
| 33.72 | 4.8 |
| 34.58 | 2.0 |
| 34.95 | 1.9 |
| 35.61 | 3.0 |
| 37.25 | 2.2 |
| 37.81 | 3.1 |

The crystalline Form II of ivabradine hydrochloride is further characterized by differential scanning calorimetry substantially as depicted in FIG. 2. It is further characterized by having one or more of endothermic peaks in the range of 73° C.-78° C., in the range of 152° C.-159° C., and in the range of 197° C.-199° C.

In another general aspect, the invention provides a novel crystalline Form III of ivabradine hydrochloride characterized by X-ray powder diffraction pattern having characteristics peaks at about 15.48°, 16.18°, 19.00°, 19.78°, 24.12°, 24.41° (2θ).

The crystalline Form III of ivabradine hydrochloride is further characterized by X-ray powder diffraction pattern having peaks substantially as depicted in FIG. 3.

The crystalline Form III of ivabradine hydrochloride is further characterized by X-ray powder diffraction pattern having characteristic peaks at degrees 2θ substantially as depicted in Table-2 as herein below.

TABLE 2

Characteristic X-ray Powder Diffraction Pattern Peaks (expressed in 2θ ± 0.2° 2θ) and Relative Intensities of Diffraction Lines for Form III of Ivabradine Hydrochloride

| Degree 2θ ± 0.2° 2θ | I/Io |
|---|---|
| 4.08 | 2.6 |
| 8.02 | 9.6 |
| 8.70 | 5.1 |
| 9.79 | 2.8 |
| 10.49 | 1.0 |
| 11.16 | 2.5 |
| 12.12 | 7.7 |
| 12.34 | 5.2 |
| 12.72 | 1.3 |
| 13.20 | 11.2 |
| 14.33 | 2.9 |
| 14.69 | 1.1 |
| 15.48 | 100.0 |
| 16.18 | 26.9 |
| 16.84 | 8.7 |
| 17.03 | 13.6 |
| 17.33 | 5.8 |
| 17.98 | 21.7 |
| 19.00 | 25.7 |
| 19.78 | 33.1 |
| 20.92 | 24.9 |
| 21.70 | 15.7 |
| 22.38 | 24.4 |
| 24.12 | 39.8 |
| 24.41 | 26.2 |
| 25.44 | 16.9 |
| 26.14 | 7.0 |
| 26.56 | 4.8 |
| 27.38 | 10.2 |
| 27.81 | 13.0 |
| 28.56 | 3.3 |
| 29.29 | 2.2 |
| 29.82 | 4.0 |
| 30.79 | 5.6 |
| 31.36 | 8.4 |
| 31.68 | 6.9 |
| 32.82 | 4.5 |
| 33.73 | 5.4 |
| 34.60 | 2.2 |
| 34.89 | 2.0 |
| 35.58 | 2.3 |
| 37.19 | 2.2 |
| 37.83 | 3.3 |
| 38.49 | 1.5 |

In another aspect, the present invention provides a process for the preparation of crystalline Form II of ivabradine hydrochloride. The process comprising: (a) providing solution of ivabradine hydrochloride in one or more suitable solvents to obtain ivabradine hydrochloride solution; and (b) obtaining the crystalline Form II of ivabradine hydrochloride by the removal of the solvents.

In general, the suitable solvent as in step (a) comprises one or more of methanol, ethanol, isopropanol, butanol, dimethylformamide, dimethylacetamide, dimethylsulfoxide, N-methylpyrrolidone, methyl ethyl ketone, acetone, methyl isobutyl ketone, ethyl acetate, butyl acetate, isopropyl acetate, acetonitrile, tetrahydrofuran, 2-methyltetrahydrofuran, 1,4-dioxane, water, or mixtures thereof. The removing of solvent as in step (b) comprises one or more of filtration, filtration under vacuum, decantation, centrifugation, distillation and distillation under vacuum.

The solution of ivabradine hydrochloride is provided in a mixture of methyl ethyl ketone and tetrahydrofuran from about ambient temperature to about reflux temperature of mixture. In particular, the solution may be heated at about 30° C. to about 120° C., more particularly from about 35° C. to about 80° C. followed by cooling. The cooled solution is subjected to removal of solvents by the know techniques as disclosed herein above.

In another general aspect, the present invention provides a process for the preparation of crystalline Form III of ivabradine hydrochloride. The process comprising: (a) contacting ivabradine hydrochloride with a preheated one or more suitable solvent to obtain ivabradine hydrochloride solution; and (b) obtaining the crystalline Form III of ivabradine hydrochloride by the removal of the solvents.

In general, the suitable solvent as in step (a) comprises one or more of dimethylformamide, dimethylacetamide, dimethylsulfoxide, N-methylpyrrolidone, acetone, methyl ethyl ketone, methyl isobutyl ketone, acetonitrile, water, or mixtures thereof. The removing of solvent as in step (b) comprises one or more of filtration, filtration under vacuum, decantation, centrifugation, distillation and distillation under vacuum.

Embodiments of the process may include one or more of the following features. For example, the solution of ivabradine hydrochloride may be obtained by heating ivabradine hydrochloride in one or more organic solvents. The solution may be seeded with one or more crystals of Form II of ivabradine hydrochloride prior to the initiation of product crystallization or the slurry may be cooled prior to filtration.

According to further embodiments, the process further comprising additional drying of the ivabradine hydrochloride obtained. The drying is carried out under for example in a hot air oven, tray drier, dried under vacuum and/or in a Fluid Bed Drier. In general, the drying comprises at a temperature of above about 40° C. in hot air oven for about 1 hour to about 12 hours. The drying may be done at about 40° C. to about 70° C. The process may include further forming of the product so obtained into a finished dosage form.

In another aspect, the present invention provides a process for the preparation of crystalline Form II of ivabradine hydrochloride, the process comprising:
(a) contacting ivabradine base with hydrogen chloride in one or more first solvents to obtain ivabradine hydrochloride;
(b) obtaining the solution of ivabradine hydrochloride in one or more second solvents to obtain ivabradine hydrochloride solution; and
(c) obtaining the crystalline Form II of ivabradine hydrochloride by the removal of second solvents.

In general, the process includes contacting ivabradine base with hydrogen chloride in one or more first solvents. The first solvent comprises one or more of methanol, ethanol, isopropanol, butanol, dimethylformamide, dimethylacetamide, dimethylsulfoxide, N-methylpyrrolidone, methyl According to another aspect, the present invention provides storage stable crystalline Form II and Form III of ivabradine hydrochloride.

In general, the storage stable crystalline Form II of ivabradine hydrochloride is substantially free from known crystalline forms β, δ, or γ. Further, the storage stable crystalline Form II of ivabradine hydrochloride is substantially free from amorphous form.

In general, the storage stable crystalline Form III of ivabradine hydrochloride is substantially free from known crystalline forms β, δ, or γ. Further, the storage stable crystalline Form II of ivabradine hydrochloride is substantially free from amorphous form.

According to another aspect, the present invention provides stable crystalline Form II of ivabradine hydrochloride, wherein the Form II of ivabradine hydrochloride is having water content from about 2.0% to about 4.0% w/w.

In another aspect, the present invention provides a process for packaging crystalline ivabradine hydrochloride, the process comprising:
(a) placing crystalline ivabradine hydrochloride under nitrogen atmosphere in a non-permeable bag and tying with a thread;
(b) placing the bag of step (a) inside a black color polyethylene bag, optionally containing oxygen busters and sealing it;
(c) placing the bag of step (b) inside a triple laminated bag, optionally containing oxygen busters and sealing it; and
(d) placing the sealed triple laminated bag inside a high density polyethylene (HDPE) container and sealing it, wherein crystalline ivabradine hydrochloride comprises of Form II or Form III.

In another general aspect, the storage stable crystalline Form-II of ivabradine hydrochloride may be characterized by atleast 6 months stability results as outline in Table-III which is representative for one of the batch.

TABLE III

| Sr. No. | Tests | Specifications | Initial | 1 Month 40° C. ± 2° C./ 75% ± 5% RH | 2 Months 40° C. ± 2° C./ 75% ± 5% RH | 3 Months 40° C. ± 2° C./ 75% ± 5% RH | 6 Months 40° C. ± 2° C./ 75% ± 5% RH |
|---|---|---|---|---|---|---|---|
| 1. | Description | White to slightly yellow powder | White Powder | White Powder | White Powder | White Powder | White Powder |
| 2. | Water by KF (% w/w) | Not more than 4.0% | 2.1 | 2.0 | 2.0 | 2.1 | 2.0 |
| 3. | Impurity Profile | | | | | | |
| | (i) Tetrahydro benzazepine | Not more than 0.15 | BDL | BDL | BDL | BDL | BDL |
| | (ii) (S)-methyl amino Compd. | Not more than 0.15 | BDL | BDL | BDL | BDL | BDL |
| | (iii) Benzocylco butane Compd. | Not more than 0.15 | BDL | BDL | BDL | BDL | BDL |
| | (iv) Dimer Impurity | Not more than 0.15 | BDL | BDL | BDL | BDL | BDL |
| | (v) Single Ind. | Not more than 0.15 | 0.04 | 0.02 | 0.02 | 0.03 | 0.03 |
| | (vi) Total Imp. | Not more than 0.15 | 0.09 | 0.05 | 0.03 | 0.08 | 0.09 |
| 4. | Polymorph | Form-II | Form-II | Form-II | Form-II | Form-II | Form-II |

BDL = Below Detection Limit ethyl ketone, acetone, methyl isobutyl ketone, ethyl acetate, butyl acetate, isopropyl acetate, acetonitrile, tetrahydrofuran, 2-methyltetrahydrofuran, 1,4-dioxane, water, or mixtures thereof.

In general, the second solvent comprises one or more of dimethylformamide, dimethylacetamide, dimethylsulfoxide, N-methylpyrrolidone, acetonitrile, tetrahydrofuran, 2-methyltetrahydrofuran, 1,4-dioxane, water, or mixtures thereof.

In another general aspect, the present invention accordingly provides a pharmaceutical composition comprising a therapeutically effective amount of crystalline Form II of ivabradine hydrochloride and one or more pharmaceutically acceptable carriers, excipients or diluents.

In another general aspect, the storage stable crystalline Form III of ivabradine hydrochloride may be characterized by atleast 6 months stability results as outline in Table-IV which is representative for one of the batch.

TABLE IV

| Sr. No. | Tests | Specifications | Initial | 1 Month 40° C. ± 2° C./ 75% ± 5% RH | 2 Months 40° C. ± 2° C./ 75% ± 5% RH | 3 Months 40° C. ± 2° C./ 75% ± 5% RH | 6 Months 40° C. ± 2° C./ 75% ± 5% RH |
|---|---|---|---|---|---|---|---|
| 1. | Description | White to slightly yellow powder | White Powder | White Powder | White Powder | White Powder | White Powder |
| 2. | Impurity Profile | | | | | | |
| | (i) Tetrahydro benzazepine | Not More than 0.15 | BDL | BDL | BDL | BDL | BDL |
| | (ii) (S)-methyl amino Compd. | Not more than 0.15 | BDL | BDL | BDL | BDL | BDL |
| | (iii) Benzocylco butane Compd. | Not more than 0.15 | BDL | BDL | BDL | BDL | BDL |
| | (iv) Dimer Impurity | Not more than 0.15 | BDL | BDL | BDL | BDL | BDL |
| | (v) Single Ind. | Not more than 0.15 | 0.04 | 0.04 | 0.03 | 0.04 | 0.03 |
| | (vi) Total Imp. | Not more than 0.15 | 0.09 | 0.07 | 0.06 | 0.08 | 0.09 |
| 4. | Polymorph | Form-III | Form-III | Form-III | Form-III | Form-III | Form-III |

BDL = Below Detection Limit

In another general aspect, the present invention accordingly provides a pharmaceutical composition comprising a therapeutically effective amount of crystalline Form III of ivabradine hydrochloride and one or more pharmaceutically acceptable carriers, excipients or diluents.

In further aspect, the present invention provides a pharmaceutical composition comprising a therapeutically effective amount of a storage stable crystalline Form II of ivabradine hydrochloride having no detectable quantity of crystalline β, δ, γ, or amorphous forms, and one or more pharmaceutically acceptable carriers, excipients, or diluents.

In further aspect, the present invention provides a pharmaceutical composition comprising a therapeutically effective amount of a storage stable crystalline Form III of ivabradine hydrochloride having no detectable quantity of crystalline β, δ, γ, or amorphous forms, and one or more pharmaceutically acceptable carriers, excipients, or diluents.

An aspect of the present application provides a pharmaceutical compositions comprising therapeutically effective amount of a crystalline Form II or Form III of ivabradine hydrochloride substantially free of one or more its corresponding impurities as measured by HPLC.

The impurities for ivabradine hydrochloride can be one or more of the following.

S-methyl amine: (S)-1-(4,5-dimethoxy-1,2-dihydrocyclobutanbenzen-1-yl)-N-methylmethamine.
Tetrahydrobenzazepine: 7,8-Dimethoxy-1,3,4,5-tetrahydro-2H-3-benzazepine-2-one.
BCP condense: (1S)-4,5-Dimethoxy-1-(methylaminomethyl)benzocyclobutane hydrochloride.
Dimer impurity: 1-(4,5-Dimethoxy-1,2-dihydrocyclobutanebenzen-1-yl)-N-((4,5-dimethoxy-1,2-dihydrocyclobutanbenzen-1-yl)methyl-N-methylmethamine.

According to one aspect there is provided a pharmaceutical composition comprising a therapeutically effective amount of crystalline forms Form II or Form III of ivabradine hydrochloride substantially free from residual methyl ethyl ketone.

An aspect of the invention provides crystalline Form II of ivabradine hydrochloride having particle size distributions wherein the 10th volume percentile particle size (D10) is less than about 50 μm, the 50th volume percentile particle size (D50) is less than about 200 μm, or the 90th volume percentile particle size (D90) is less than about 400 μm, or any combination thereof.

An aspect of the invention provides crystalline Form III of ivabradine hydrochloride having particle size distributions wherein the 10th volume percentile particle size (D10) is less than about 50 μm, the 50th volume percentile particle size (D50) is less than about 200 μm, or the 90th volume percentile particle size (D90) is less than about 400 μm, or any combination thereof.

In another aspect, the invention provides a process for the preparation of ivabradine hydrochloride which may be used starting material.

In general, the process for preparation of ivabradine hydrochloride includes a mixing ivabradine hydrochloride with one or more of suitable solvent comprises tetrahydrofuran (THF), dimethylsulfoxide (DMSO), dimethylformamide, diethylether, dimethylether, water or a mixture thereof.

Embodiments of the process includes providing mixture of ivabradine hydrochloride, tetrahydrofuran (THF) and water under heating conditions until dissolution is complete and the solution may be further cooled until crystallization is complete, and the product may be collected by filtration. The product thus obtain may be dried to obtain of ivabradine hydrochloride or used as such for the further process steps to obtain crystalline Form II or Form III.

The novel crystalline forms of ivabradine hydrochloride can be characterized by any of the analytical technique like PXRD, DSC, IR as follows:

(a) Characterization by PXRD

The X-ray powder diffraction spectrum was measured under the following experimental conditions:

Instrument: X-Ray Diffractometer, D/Max-2200/PC Make: Rigaku, Japan.
X-Ray: Cu/40 kv/40 mA
Diverging: 1°
Scattering Slit: 1°
Receiving Slit: 0.15 mm
Monochromator RS: 0.8 mm
Counter: Scintillation Counter
Scan Mode: Continuous
Scan Speed: 3,000°/Min
Sampling Width: 0.020

Scan Axes: Two Theta/Theta
Scan Range: 2.000° to 40,000°
Theta Offset: 0.000°
(b) Characterization by Differential Scanning Calorimetry (DSC)

Analytical method: Differential scanning calorimetric analysis was performed using a Perkin Elmer Diamond DSC control unit and a DSC 300° C. differential scanning calorimeter. 2-5 mg samples were placed in crimped aluminum pans and heated from 50° C. to 300° C. in a liquid nitrogen atmosphere at a heating rate of 10° C./minute. Zinc-Indium was used as the standard substance.

The present invention is further illustrated by the following examples which are provided merely to be exemplary of the invention and do not limit the scope of the invention. Certain modification and equivalents will be apparent to those skilled in the art and are intended to be included within the scope of the present invention.

EXAMPLE 1

Preparation of Ivabradine Hydrochloride (I)

100 g of ivabradine base and 300 mL acetonitrile were cooled to 0° C. to 5° C. and acetonitrile hydrochloric acid solution was added drop wise by adjusting the pH to about 1-2. The resulting mass was stirred till complete precipitation and maintained for 60 minutes. The product was filtered under nitrogen and washed with chilled acetonitrile. The wet-cake and acetonitrile were heated at 60-65° C. and stirred for 30 min. The reaction mixture was gradually cooled to 25° C. and stirred for 1 hour. The product was filtered under vacuum and nitrogen atmosphere. The wet-cake was washed with chilled acetonitrile. The product was dried under vacuum at 50-55° C. to obtain 75% 80 g crude ivabradine hydrochloride. The product was packed in double polyethene bag under nitrogen.

EXAMPLE 2

Preparation of Ivabradine Hydrochloride (I)

100 g of ivabradine hydrochloride crude and 450 mL of THF were heated at 60-65° C. 50 mL of water was added drop wise to get a clear solution at 60-65° C. The reaction mixture was stirred for 30 minutes at the same temperature and cooled slowly to 20-25° C. The reaction mixture was stirred for 1.5 hour and filtered. The wet-cake was washed with THF and suck dried under nitrogen for 30 min. The wet-cake and 450 mL THF were heated again to get a clear solution at 60-65° C. and stirred for 30 min. The reaction mixture was cooled at 25° C. and stirred for 1.5 hour. The product thus obtained was filtered to obtain 110 g wet-cake, which was used as such for the preparation of Form-II or Form-III.

EXAMPLE 3

Preparation of Crystalline Form II of Ivabradine Hydrochloride (I)

20 g of ivabradine hydrochloride wet-cake and 200 mL of methyl ethyl ketone and tetrahydrofuran (10 mL) were heated at 75-80° C. for 15 minutes to get a clear solution. The reaction mixture was stirred for further 60 minutes and cooled to 25° C. gradually. The reaction mixture was stirred for 2 hours and filtered. The wet-cake was washed with methylethyl ketone and dried under vacuum at 40° C. to 45° C. for 12 hours. The X-ray powder diffraction discloses Form-II. (FIG. 1) and DSC (FIG. 2).

EXAMPLE 4

Preparation of Crystalline Form II of Ivabradine Hydrochloride (I)

25 g of ivabradine hydrochloride wet-cake and 250 mL of methyl ethyl ketone and 12.5 mL tetrahydrofuran were heated at 40° C. for 15 minutes to obtain solution. The reaction mixture was stirred for further 60 minutes and cooled to 25° C. gradually. The reaction mixture was stirred for 2 hours and filtered. The wet-cake was washed with methylethyl ketone and dried under vacuum at 40° C. to 45° C. for 12 hours. The X-ray powder diffraction discloses Form-II. (FIG. 1) and DSC (FIG. 2).

EXAMPLE 5

Preparation of Crystalline Form III of Ivabradine Hydrochloride (I)

200 mL of methyl ethyl ketone was charged in a round bottom flask and the temperature was raised to 50-60° C. 20.0 g of ivabradine hydrochloride was added and subsequently stirred for about 15 min at 50-60° C. The reaction mixture was then refluxed at 75-80° C. to obtain clear solution. The reaction mixture was allowed to cool gradually and stirred for 2 hours and filtered. The wet-cake was washed with 20 mL of methyl ethyl ketone and dried under vacuum at 40° C. to 45° C. for 12 hours. The X-ray powder diffraction discloses Form-III. (FIG. 3).

EXAMPLE 5

Packing of Crystalline Forms—Form II & Form III of Ivabradine Hydrochloride (I)

The crystalline polymorph Form II & Form III of ivabradine hydrochloride obtained as per example-3 and 4 was stored under nitrogen atmosphere and packed in a non-permeable bag tied with a thread, keeping primary packing inside a black color polyethylene bag containing oxygen busters and sealing it, placing above the non-permeable bag inside a triple laminated bag containing oxygen busters and sealing it, and placing the sealed triple laminated bag inside a closed high density polyethylene (HDPE) container.

While the present invention has been described in terms of its specific embodiments, certain modifications and equivalents will be apparent to those skilled in the art and are intended to be included within the scope of the present invention.

We claim:
1. A crystalline Form II of ivabradine hydrochloride characterized by x-ray powder diffraction having characteristic peaks at about 15.50°, 18.02°, 19.00°, 19.80°, 22.42°, 24.16°, and 25.46°±0.2° (2θ), substantially free from one or more of: (S)-1-(4,5-dimethoxy-1,2-dihydrocyclobutanbenzene-1-yl)-N-methylmethamine (S-methylamine); 7,8-dimethoxy-1,3,4,5-tetrahydro-2H-3-benzazepine-2-one (tetrahydrobenzazepine); (1S)-4,5-dimethoxy-1-(methylaminomethyl)benzocyclobutane hydrochloride (BCP condense); or (1S)-4,5-dimethoxy-1,2-dihydrocyclobutanebenzen-1-yl)-N-((4,5-dimethoxy-1,2-dihydrocy- clobutanebenzen-1-yl)methyl-N-methyl-methamine (dimer impurity), as measured by area percentage of HPLC.

2. The crystalline ivabradine hydrochloride according to claim 1, wherein single individual impurity is not more than 0.15%, as measured by area percentage of HPLC.

3. The crystalline ivabradine hydrochloride according to claim 1, wherein the total impurities is not more than 0.15%, as measured by area percentage of HPLC.

4. The crystalline ivabradine hydrochloride according to claim 1, having a purity of about 99% or more, as measured by area percentage of HPLC.

5. The crystalline ivabradine hydrochloride according to claim 1, which is substantially free from known crystalline forms β, δ, γ, or amorphous forms after storage for 6 months at 40° C. and a relative humidity of 75% or at 25° C. and a relative humidity of 60%.

6. The crystalline ivabradine hydrochloride according to claim 1, which is having particle size distributions wherein the 10th volume percentile particle size (D10) is less than about 50 μm, the 50th volume percentile particle size (D50) is less than about 200 μm, or the 90$^{th}$ volume percentile particle size (D90) is less than about 400 μm, or any combination thereof.

7. The crystalline ivabradine hydrochloride according to claim 5, comprising a packaging which includes placing crystalline ivabradine hydrochloride under nitrogen atmosphere in a non-permeable bag or placing crystalline ivabradine hydrochloride in polyethylene bag, optionally containing oxygen busters and sealing it or placing crystalline ivabradine hydrochloride in a triple laminated bag, optionally containing oxygen busters and sealing it or placing crystalline ivabradine hydrochloride in triple laminated bag inside a high density polyethylene (HDPE) container.

8. A pharmaceutical composition comprising crystalline Form II of ivabradine hydrochloride characterized by x-ray powder diffraction having characteristic peaks at about 15.50°, 18.02°, 19.00°, 19.80°, 22.42°, 24.16°, and 25.46°±0.2° (2θ)having purity of about 99% or more and substantially free from one or more of: (S)-1-(4,5-dimethoxy-1,2-dihydrocyclobutanbenzene-1-yl)-N-methylmethamine (S-methylamine); 7,8-dimethoxy-1,3,4,5-tetrahydro-2H-3-benzazepine-2-one (tetrahydrobenzazepine); (1S)-4,5-dimethoxy-1-(methylaminomethyl)benzocyclobutane hydrochloride (BCP condense); or (1S)-4,5-dimethoxy-1,2-dihydrocyclobutanebenzen-1-yl)-N-((4,5-dimethoxy-1,2-dihydrocyclobutane-benzen-1-yl)methyl-N-methyl-methamine (dimer impurity), as measured by area percentage of HPLC.

9. The pharmaceutical composition according to claim 8, wherein the crystalline ivabradine hydrochloride is crystalline Form II characterized by x-ray powder diffraction having characteristic peaks at about 15.50°, 18.02°, 19.00°, 19.80°, 22.42°, 24.16°, and 25.46°±0.2° (2θ).

10. The crystalline ivabradine hydrochloride according to claim 1, is prepared by the process comprising:
    (a) providing a solution of ivabradine hydrochloride in one or more solvents by heating at about 30° C. to about 120° C.;
    (b) obtaining the crystalline Form II of ivabradine hydrochloride by the removal of the solvents; and
    (c) drying the crystalline Form II of ivabradine hydrochloride at about 40° C. to about 70° C., wherein the solvent is at least one member selected from the group consisting of methanol, ethanol, isopropanol, butanol, dimethylformamide, dimethylacetamide, dimethylsulfoxide, N-methylpyrrolidone, methyl ethyl ketone, acetone, methyl isobutyl ketone, ethyl acetate, butyl acetate, isopropyl acetate, acetonitrile, tetrahydrofuran, 2-methyltetrahydrofuran, 1,4-dioxane, water and mixtures thereof.

11. The process according to claim 10, wherein the removal of the solvent comprises one or more of filtration, filtration under vacuum, decantation, centrifugation, distillation and distillation under vacuum.

12. A process for preparing crystalline ivabradine hydrochloride according to claim 1, the process comprising:
    (a) contacting ivabradine base with hydrogen chloride in one or more first solvents to obtain ivabradine hydrochloride;
    (b) obtaining a solution of ivabradine hydrochloride in one or more second solvents;
    (c) optionally adding water to the solution, heating the solution and cooling to obtain the ivabradine hydrochloride wet-cake; and
    (d) treating the wet-cake with one or more of first solvents to obtain the crystalline of ivabradine hydrochloride.

13. The process according to claim 12, wherein the first is at least one member selected from the group consisting of methanol, ethanol, isopropanol, butanol, dimethylformamide, dimethyl acetamide, dimethylsulfoxide, N-methylpyrrolidone, methyl ethyl ketone, acetone, methyl isobutyl ketone, ethyl acetate, butyl acetate, isopropyl acetate, acetonitrile, tetrahydrofuran, 2-methyl tetrahydrofuran, 1,4-dioxane, water, or mixtures thereof.

14. The process according to claim 12, wherein the second solvent comprises one or more of dimethylformamide, dimethylacetamide, dimethylsulfoxide, N-methylpyrrolidone, acetonitrile, tetrahydrofuran, 2-methyltetrahydrofuran, 1,4-dioxane, water, or mixtures thereof.

15. A pharmaceutical composition comprising a crystalline ivabradine hydrochloride according to claim 1 having one or more pharmaceutically acceptable carriers, excipients, or diluents.

16. The pharmaceutical composition according to claim 8 having one or more pharmaceutically acceptable carriers, excipients, or diluents.

* * * * *